US007872159B2

(12) United States Patent
Peterson et al.

(10) Patent No.: US 7,872,159 B2
(45) Date of Patent: *Jan. 18, 2011

(54) CHEMICAL PRODUCTION PROCESSES, SYSTEMS, AND CATALYST COMPOSITIONS

(75) Inventors: Thomas H. Peterson, Midland, MI (US); Alan H. Zacher, Pasco, WA (US); Michel J. Gray, Pasco, WA (US); James F. White, Richland, WA (US); Todd A. Werpy, West Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/895,362

(22) Filed: Aug. 24, 2007

(65) Prior Publication Data

US 2009/0054693 A1      Feb. 26, 2009

Related U.S. Application Data

(63) Continuation-in-part of application No. 11/895,593, filed on Aug. 24, 2007, and a continuation-in-part of application No. 11/895,414, filed on Aug. 24, 2007, and a continuation-in-part of application No. 11/895,592, filed on Aug. 24, 2007, now abandoned.

(51) Int. Cl.
*C07C 45/51* (2006.01)
*C07C 45/52* (2006.01)
(52) U.S. Cl. .................................................. 568/486
(58) Field of Classification Search ................ 568/485, 568/486
See application file for complete search history.

(56) References Cited

U.S. PATENT DOCUMENTS

| | | | |
|---|---|---|---|
| 2,516,627 | A | 7/1950 | Hearne et al. |
| 2,558,520 | A | 6/1951 | Hoyt et al. |
| 3,197,483 | A | 7/1965 | Buchholz et al. |
| 3,893,946 | A | 7/1975 | Weisang et al. |
| 4,137,271 | A | 1/1979 | Stiles et al. |
| 4,234,752 | A | 11/1980 | Wu et al. |
| 4,642,394 | A | 2/1987 | Che |
| 4,729,978 | A | 3/1988 | Sawicki |
| 5,387,720 | A * | 2/1995 | Neher et al. ............... 568/486 |
| 5,426,249 | A | 6/1995 | Haas et al. |
| 5,753,716 | A | 5/1998 | Peng et al. |
| 7,683,220 | B2 * | 3/2010 | Matsunami et al. ......... 568/485 |
| 2003/0149283 | A1 | 8/2003 | Manzer |
| 2008/0214880 | A1 | 9/2008 | Dubois et al. |
| 2009/0118549 | A1 * | 5/2009 | Matsunami et al. ......... 568/486 |

FOREIGN PATENT DOCUMENTS

| | | |
|---|---|---|
| DE | 850 608 C | 9/1952 |
| DE | 23 25 051 | 12/1974 |
| DE | 42 38 493 C1 | 4/1994 |
| EP | 0509927 | 10/1992 |
| EP | 0 598 228 A1 | 10/1993 |
| EP | 0 598 229 A1 | 10/1993 |
| EP | 1 044 949 A1 | 10/2000 |
| FR | 695 931 A | 12/1930 |
| FR | 846063 | 9/1939 |
| GB | 2 093 060 A | 8/1982 |
| JP | 60 096513 | 5/1985 |
| JP | 2005213225 | 8/2005 |
| WO | WO 93/05006 | 3/1993 |
| WO | WO 99/05085 | 2/1999 |
| WO | WO 2006/087083 A2 | 8/2006 |
| WO | WO2006/114506 A | 11/2006 |
| WO | WO2007/058221 A1 | 5/2007 |
| WO | WO 2008/052993 A2 | 5/2008 |
| WO | PCT/US2008/074094 | 2/2009 |
| WO | PCT/US2008/074079 | 3/2009 |
| WO | PCT/US2008/074084 | 5/2009 |
| WO | US2008/074090 | 5/2009 |
| WO | PCT/US2008/074090 | 7/2009 |
| WO | PCT/US2008/074084 | 10/2009 |

OTHER PUBLICATIONS

Erlenmeyer et al., "Die Dissociation des Glycerins" Annalen Der Chemie, 1904, pp. 209-223.
Adkins et al., "Acrolein", Organic Syntheses, vol. 1 p. 6 1926, vol. 1 p. 15 1941, 4 pages.
Anon., "Modeling the reaction behavior of glycerol in sub- and supercritical water", Germany, 2000, 2 pgs.
Antal, Jr et al., "Heterolysis and Homolysis in Supercritical Water" American Chemical Society, 1985, pp. 78-87.
Barrault et al., "Selective Esterification . . . ", Chemical Industries, 1998, pp. 13-23.
Clacens et al. "Selective etherification of glycerol to polyglycerols . . . ", Applied Catalysis, 2002, pp. 181-190.
Cottin et al. "Preparation de diglycerol et triglycerol . . . ", Fondmental, Oct. 1998, pp. 407-412.
Delaby, "Academie Des Sciences" Comptes Rendus, 1923, pp. 690-693.
Hanyu et al., "Manfacture of Acrolein", Journal of the Osciety of Chemical Industry, Japan, vol. 37 1934, p. 538.
Hauschild et al. "Contribution a l'etude de la deshydratation . . . ", Bulletin de la Societe Chimique de France, 1956, pp. 878-881.
Ishikawa et al., "Generation of Trace Amount of Acrolein Standard . . . ", Bunseki Kagaku, The Japan Society for Analytical Chemistry, vol. 32 Oct. 1983, pp. E321-E325.
Krammer et al., "Untersuchungen zum Synthese-potential . . . ", Chemie Ingenieur Technik, 1998, pp. 1559-1563.

(Continued)

*Primary Examiner*—Sikarl A Witherspoon
(74) *Attorney, Agent, or Firm*—Wells St. John P.S.

(57) ABSTRACT

Chemical production processes are provided that can include exposing a reactant composition to a catalyst composition to form a product composition. Catalyst compositions are also provided that can include metal phosphate compositions, metal phosphorous compositions, and/or solid support compositions with the solid support compositions including one or more of $F$—$Al_2O_3$, $ZrO_2$—$CO_2$, $SiO_2$—$Al_2O_3$—$CO_2$, $SiO_2$ $Al_2O_3$, Alundum, and Silica such as Ludox AS-30.

15 Claims, 7 Drawing Sheets

OTHER PUBLICATIONS

Moureu et al., "Memoires et Communications", Comptes Rendus, 1919, pp. 885-889.

Ott et al., "Catalytic dehydration of glycerol . . . ", The Royal Society of Chemistry, 2006, pp. 214-220.

Ott et al., Chemie Ingenieur Technik, 2004, p. 1292.

Ramayya et al., "Acid-catalysed dehydration of alcohols in supercritical water", Fuel, Oct. 1987, vol. 66, pp. 1364-1371.

Rosenthaler, L., "Beitrage zum Nachnveis organischer Verbindungen", Pharmazeutische Zeitung-Nachrichten, 1954, pp. 464-466.

Sabatier et al., "Conformement A Une Decision De L'Accademie" Comptes Rendus, 1918, pp. 1003-1039.

Waldmann et al., "Uber die Dehydratisierung . . . "Chemische Berichte, 1950, pp. 287-291.

Zhukov et al., "Definition of an Effective Catalyst in the Condensation of Glycerol", Applied Chemistry of USSR, Apr. 1980, pp. 780-783.

Corma et al. Jour of Catalysis 247 (2007) 307-27.

Ott et al., "Catalytic dehydration of glycerol . . . ", Green Chem., 2006, 8, 214-220.

Tsukuda et al. CatComm 8 (2007) 1349-1353.

Chai et al, "Sustainable production of acrolein: Gas-phase dehydration of glycerol over Nb2O5 catalyst" Journal of Catalysis, Academic Press, Duluth, MN, US, vol. 250, No. 2, Aug. 14, 2007, pp. 342-349, XP022200532.

Faro, A.C. et al, "Cumene hydrocracking and tiophene HDS on niobia-supported Ni, Mo and Ni-Mo catalysts" Catalysis Today, vol. 118, 2006, pp. 402-409, XP002511927.

Mishra, T. et al, "Transition metal promoted A1PO4 catalyst 2. The catalytic activity of M0.05A10.95P04 for alchohol conversion adn cumene cracking/dehydrogenation reactions" Applied Catalysis A: General, vol. 166, 1998, pp. 115-122, XP002511925.

Song, L. et al, "A new route to prepare supported nickel phosphide/silica-alumina hydrotreating catalysts from amorphous alloys" Catalysis Today, vol. 125, Apr. 8, 2007, pp. 137-142, XP002511926.

Tsukuda et al, "Production of acrolein from glycerol over silica-supported heteropoly acids" Jul. 21, 2007, Catalysis Communications, Elsevier Science, Amsterdam, NL, pp. 1349-1353, XP022162877.

Database CA, Xu, Bo-Qing et al: "Process for dehydration of polyhydric alcohols" (XP-002524780), Nippon Shokubai Co., Ltd., Japan (Chemical Abstracts Service, Columbus, OH).

US2008/074079 IPRP, Feb. 24, 2010, Battelle Memorial Institute.
US2008/074084 IPRP, Feb. 24, 2010, Battelle Memorial Institute.
US2008/074090 IPRP, Feb. 24, 2010, Battelle Memorial Institute.
US2008/074094 IPRP, Feb. 24, 2010, Battelle Memorial Institute.

* cited by examiner

CHEMICAL PRODUCTION PROCESSES, SYSTEMS, AND CATALYST COMPOSITIONS

RELATED PATENT DATA

This application is a continuation in part of U.S. patent application Ser. No. 11/895,593, entitled Chemical Production Processes, Systems, and Catalyst Compositions by Peterson et al. which was filed on Aug. 24, 2007; Ser. No. 11/895,414, entitled Chemical Production Processes, Systems, and Catalyst Compositions by Peterson et al. which was filed on Aug. 24, 2007; Ser. No. 11/895,592, entitled Chemical Production Processes, Systems, and Catalyst Compositions by Peterson et al. which was filed on Aug. 24, 2007 now abandoned; the entirety of all of which are incorporated by reference herein.

TECHNICAL FIELD

The present disclosure relates to chemical production processes, systems, and catalyst compositions.

BACKGROUND OF THE DISCLOSURE

For nearly a century, scientists have struggled with the efficient dehydration of multihydric alcohol compounds. For example, the dehydration of glycerol to acrolein, acetol, and glycerol oligomers was first reported by Nef in 1904. When compositions were heated to temperatures between 430° C. and 450° C., carbonaceous materials and a distillate were produced that contained acrolein, acetol, water, and formaldehyde among other products. Over the next 100 years, occasional reports of catalyzed conversions of glycerol had been communicated targeting conversion to acrolein and acetol directly. As an example, the condensation of glycerol to di-, tri-, and oligoglycerol ethers had been effected with basic catalysts. However, when acidic catalysts were employed, acrolein is formed as a major by-product. As another example, acrolein has also been reported as a product of castor oil hydrolysis and cracking. Conversion of multihydric alcohol compounds has been performed in the temperature range of 250° C. to 400° C., utilizing phosphate or sulfate acid or acid salt as a catalyst. However, clays, zeolites, $CO_2$ or autoionization of supercritical $H_2O$ has been shown to effect dehydration with the yields of acrolein rarely exceeding 70%.

While examples of glycerol to acrolein transformation do exist, they are relatively few in number. As recently as 1994, U.S., Japanese, and European patents have been awarded describing the conversion of glycerol to acrolein and acrolein hydrogenation to a mixture of isomeric propanediols. In 1998, platinum bisphosphine complexes were used in the presence of strong acids and syn gas to carry out the conversion of glycerol to acrolein in 80% yield. More recently, glycerol dehydration in subcritical water catalyzed by $ZnSO_4$ in a staged reactor process has been utilized to convert glycerol to acrolein and acrylic acid. To date, processes having high selectivity and commercial viability are still not known for the conversion of glycerol to acrolein.

SUMMARY OF THE DISCLOSURE

Chemical production processes are provided that can include exposing a reactant composition to a catalyst composition to form a product composition. The reactant composition comprises a multihydric alcohol compound and the product composition comprises a carbonyl compound.

Embodiments of the process can utilize catalyst compositions such as metal phosphate compositions, metal phosphorous compositions, and/or solid support compositions with the solid support compositions including one or more of $F$—$Al_2O_3$, $ZrO_2$—$CO_2$, $SiO_2$—$Al_2O_3$—$CO_2$, $SiO_2$ $Al_2O_3$, Alundum, and silica such as Ludox AS-30.

Dehydration catalyst compositions are also provided that can include a metal phosphate composition with the metal phosphate composition including one or more elements of groups 2-7 and 9-12 of the periodic table of elements. Catalyst compositions can also include a metal phosphorous composition with the metal phosphorous composition including one or more of Si and Ti. Additional catalyst compositions can include a solid support composition with the solid support composition comprising one or more of $F$—$Al_2O_3$, $ZrO_2$—$CO_2$, $SiO_2$—$Al_2O_3$—$CO_2$, $SiO_2$—$Al_2O_3$, Alundum, and silica such as Ludox AS-30.

Chemical production systems are also provided that can include a reactant reservoir coupled to a reactor. The reactor can contain a catalyst comprising a metal phosphate composition, and/or a metal phosphorous composition, for example.

BRIEF DESCRIPTION OF THE DRAWINGS

Preferred embodiments of the disclosure are described below with reference to the following accompanying drawings.

DETAILED DESCRIPTION

This disclosure is submitted in furtherance of the constitutional purposes of the U.S. Patent Laws "to promote the progress of science and useful arts" (Article 1, Section 8).

Figure 1:
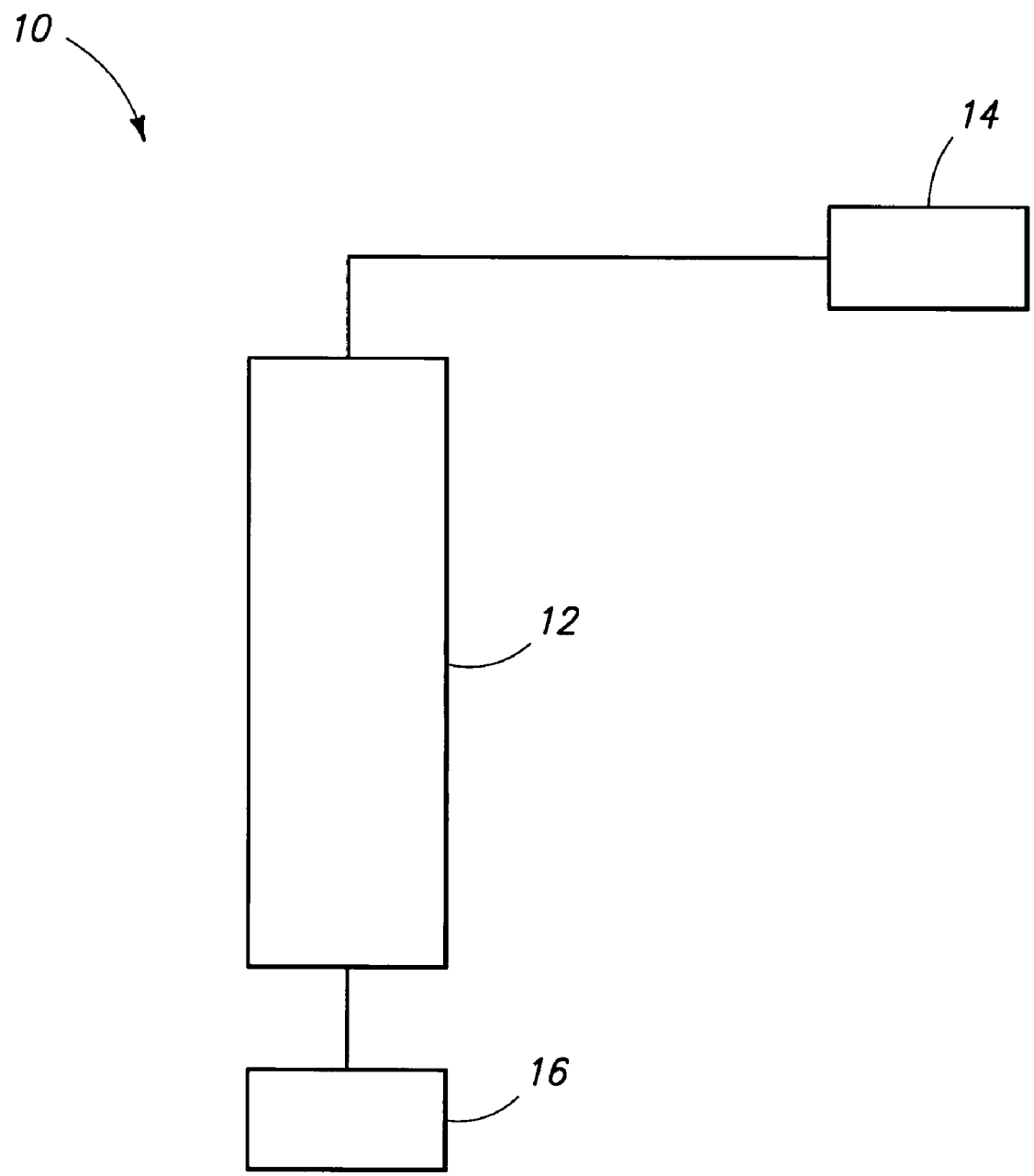
FIG. 1 is a chemical production system according to an embodiment of the disclosure.

The chemical production processes of the present disclosure will be described with reference to FIGS. 1-7. Referring first to FIG. 1, a chemical production process system 10 is shown that includes a reactor 12 coupled to both a reactant reservoir 14 and a product reservoir 16. In accordance with the present disclosure, reactant reservoir 14 can be coupled to reactor 12 utilizing conduits that facilitate the flow of reactant from reactant reservoir 14 to reactor 12. This flow can be facilitated utilizing pressure differentials between reactant reservoir 14 and reactor 12. For example, these pressure differentials can be facilitated utilizing pumps to provide a pressure differential between reactant reservoir 14 and reactor 12. The reactant within reactant reservoir 14 can be a multihydric alcohol compound. An example multihydric alcohol compound can include the compound glycerol, which when dehydrated can result in a product composition that includes one or both of acrolein and/or acetol, for example.

Reactor 12 can include a housing that can be configured to house a catalyst and be utilized to facilitate the exposure of the reactant within reactant reservoir 14 to catalyst within reactor 12. The catalyst can be supported and/or unsupported catalyst, for example. Unsupported catalysts can be referred to as bulk catalysts. Reactor 12 can be jacketed or can be configured as a fluidized bed reactor, for example.

The product composition provided to product reservoir 16 can be a dehydration product of the multihydric alcohol compound such as a carbonyl compound. The pressure differential apparatus used to facilitate the transfer of reactant from reactant reservoir 14 can also be utilized to provide product from reactor 12 to product reservoir 16. In accordance with an example embodiment, system 10 can be configured to expose a multihydric alcohol compound such as glycerol from reservoir 14 to a catalyst composition within reactor 12 to form a product composition including one or both of acrolein and acetol.

Figure 2:
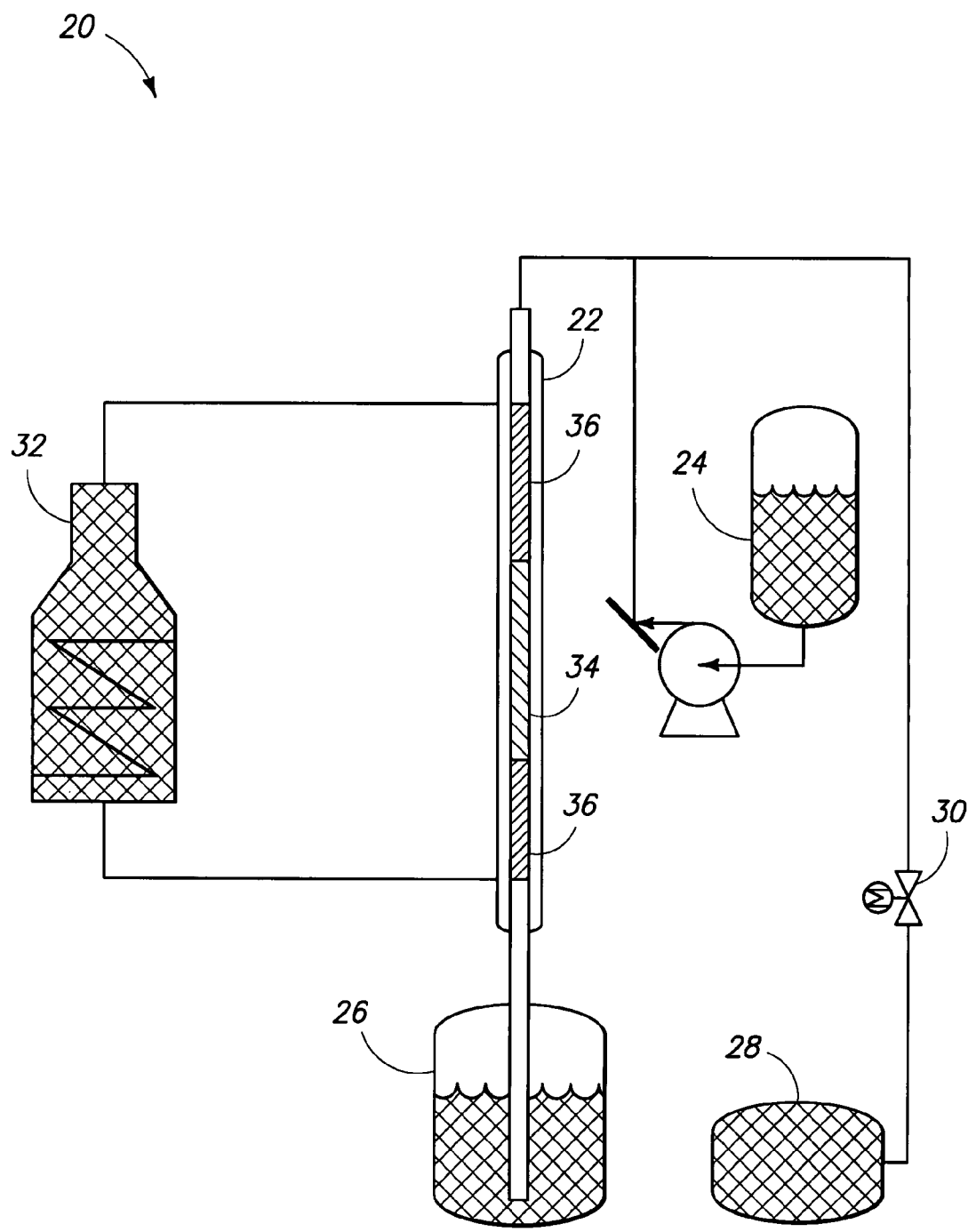
FIG. 2 is a chemical production system according to another embodiment of the disclosure.
Figure 3:
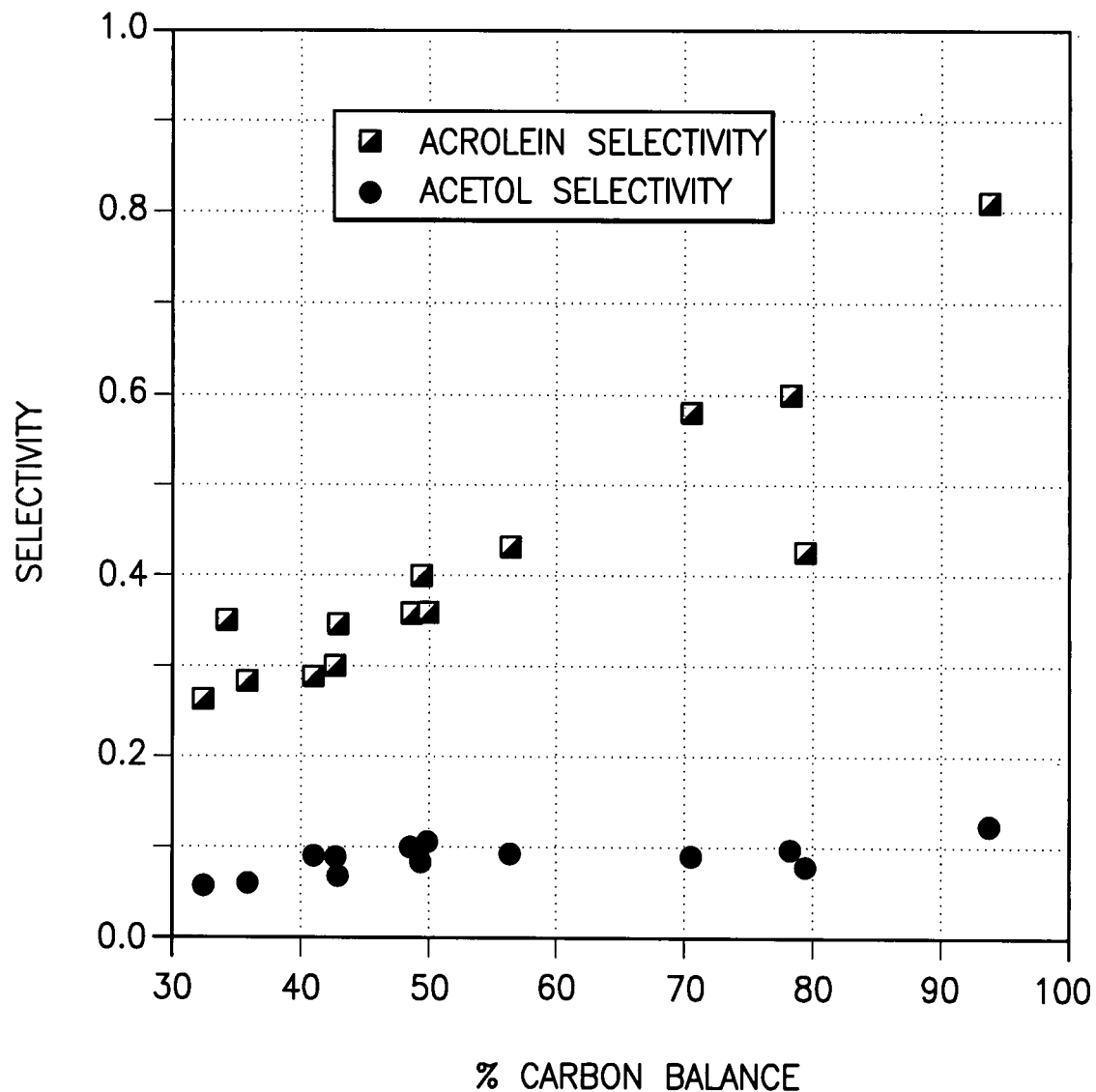
FIG. 3 is a plot of data acquired utilizing an embodiment of the disclosure.

In accordance with another embodiment, FIG. 2 depicts a chemical production system 20 that includes a reactor 22 coupled to a reactant reservoir 24 as well as a product reservoir 26. Reactant of reactant reservoir 24 can be a multihydric alcohol compound, for example. To facilitate the flow of reactant from reactant reservoir 24 to reactor 22, a carrier composition 28 including a gas or liquid such as nitrogen is provided to a reactant reservoir conduit utilizing flow control 30. In accordance with another embodiment $CO_2$ can be utilized as the carrier composition 28. These solid support beds were also treated with $CO_2$ and reactant from reactor reservoir 24 can be combined with carrier composition 28 and provided to reactor 22.

Reactor 22 can be configured as an oil heated reactor utilizing an oil heater 32. Reactor 22 can be configured having a catalyst 34 supported by packing material 36. Catalyst 34 can be solid support materials including silica, silica alumina zirconia, and acidic fluoride-treated alumina, for example. More particularly, catalyst 34 can be a solid support composition such as one or more of F—$Al_2O_3$, $ZrO_2$—$CO_2$, $SiO_2$—$Al_2O_3$—$CO_2$, $SiO_2$—$Al_2O_3$, Alundum, and Silica such as Ludox AS-30. Packing material 36 can include quartz wool. In accordance with one example, glycerol from reactant reservoir 24 can be provided with carrier composition 28 to reactor 22 and exposed to catalyst 34 such as solid support materials. A temperature within reactor 24 during exposure of reactant to these solid support materials can be in the range of about 275° C. to about 335° C. or 300° C. to about 335° C., using residence times of 250 to 300 milliseconds. Prior to exposing reactant to catalyst 34, catalyst 34 can be exposed to carrier composition 28 such as $CO_2$. Table 1 below is an indication of the results of the utilization of these solid supports at various reactor temperatures.

can be employed utilizing helium as carrier gas at a 2.61 mL/min flow rate. Injections of 1 μL utilizing a 25:1 split ratio can be made with the injector port maintained at 250° C. Oven temperature programming can utilize an initial temperature of 40° C. with a hold for 5 minutes followed by a 10° C./min ramp to 245° C. and a hold at the final temperature for 4.5 minutes. Calibrations can be performed on a periodic or monthly basis using known standard solutions for glycerol, acrolein, and acetol. Calibrations can take place using a series of five standard solutions prepared by serial dilution to determine the linear response for each compound, and acceptance of each curve determined if the linear response had an R value of greater than 0.99.

Liquid chromatographic analyses can be carried out on a Waters LC system incorporating a Waters 515 pump, Waters 2410 Refractive Index Detector (RID), and a Waters 717 plus Autosampler for sample introduction. Analyses can be performed utilizing Empower Pro Software. Separations of 10 μL injections can be effected on an Aminex HPX-87H Organic Acid Analysis column operated at 35° C. and employing a 0.005M $H_2SO_4$ as the eluent with a flow rate of 0.55 mL/min. Total run times of 45 minutes were sufficient to elute all compounds of interest. Calibration curves can be prepared as described for GC calibrations and using the same set of standard solutions used for GC calibration.

Referring to product reservoir 26 of system 20, upon exiting reactor 22, product can be acquired by time collection of reactor 22 effluent in a known quantity of a chilled scrub solution containing 1 wt % n-BuOH with mass balances for a given reactor run determined by a ratio of collected effluent mass to expected mass based on feed rate and run time. For example, two small aliquots can be removed and diluted to concentrations appropriate for GC and LC analyses. The diluted samples can then be analyzed as described previously and wt % compositions determined from calibrated detector responses used to determine absolute compositions of the collected effluent. The use of known quantities of n-BuOH in the scrub solutions can permit a primary check of analytical sampling technique. Reported values for conversion, yield, selectivity, and carbon balance present averages of those val-

TABLE 1

Examination of support materials for glycerol dehydration at 300-335° C.

| Catalyst Description | T (° C.) | Mass Bal. % | Carbon Bal. % | % Conv | Acrolein Yield % | Acrolein Selectivity | Acetol Selectivity |
|---|---|---|---|---|---|---|---|
| fluoride treated $Al_2O_3$ | 300 | 107.17 | 83.52 | 51.16 | 23.66 | 0.462 | 0.215 |
| $ZrO_2$—$CO_2$ | | 87.81 | 99.26 | 3.70 | 1.23 | 0.332 | 0.469 |
| $SiO_2$—$Al_2O_3$—$CO_2$ | | 103.26 | 59.71 | 93.89 | 37.96 | 0.404 | 0.167 |
| $SiO_2$—$Al_2O_3$ | | 104.94 | 104.67 | 41.38 | 37.32 | 0.902 | 0.211 |
| Alundum | | 70.36 | 70.40 | 29.68 | 0.08 | 0.003 | 0.000 |
| Silica derived from Ludox AS-30 | | 99.23 | 94.63 | 5.37 | 0.00 | 0.000 | 0.000 |
| fluoride treated $Al_2O_3$ | 320 | 101.69 | 62.16 | 98.98 | 43.56 | 0.440 | 0.178 |
| $ZrO_2$—$CO_2$ | | 98.98 | 93.69 | 12.63 | 2.3 | 0.182 | 0.319 |
| $SiO_2$—$Al_2O_3$—$CO_2$ | | 103.87 | 62.38 | 99.34 | 44.17 | 0.445 | 0.177 |
| $SiO_2$—$Al_2O_3$ | | 108.92 | 94.60 | 81.31 | 60.73 | 0.747 | 0.187 |
| Alundum | | 100.75 | 98.32 | 1.68 | 0.00 | 0.000 | 0.000 |
| $ZrO_2$—$CO_2$ | 335 | 87.20 | 69.77 | 48.39 | 6.30 | 0.130 | 0.245 |
| $SiO_2$—$Al_2O_3$ | | 97.60 | 56.84 | 94.92 | 39.61 | 0.417 | 0.128 |

The qualitative and quantitative data of Table 1 above as well as all remaining data of the present application can be acquired utilizing gas and liquid chromatography techniques. For example, gas chromatographic analyses can be performed utilizing a Shimadzu GC-2010 Gas Chromatograph (GC) equipped with a Flame Ionization Detection (FID) operating at 280° C., and an AOC-20 autosampler, and employing GC Solutions Software. A DB-WAX (J & W Scientific) capillary column (30 m×0.32 mm I.D.×0.25 μm film thickness)

ues determined by both GC and LC analyses. Glycerol conversion can be calculated by the differences between calculated quantity of glycerol feed (based on feed rate and run time) and the quantity of glycerol collected in the reactor effluent and may be uncertain when mass balances are not satisfactory. Values exclude any experimental runs that did not provide mass balances between 90% and 100%. Product yields can be calculated by the ratio of quantity of product formed to the quantity of glycerol. Product selectivities can be calculated from the quantity of product formed divided by the quantity of glycerol converted. Carbon balances can be calculated from the sum of the molar quantities of glycerol, acrolein, and acetol components divided by the molar quantity of glycerol fed. Liquid Chromatographic techniques can permit the quantification of formic acid and acetic acid by-products. However, since their combined quantity rarely exceeded 3%, their presence was not included in carbon balance determination.

According to another embodiment, and referring to FIG. 2, catalyst 34 can include a metal phosphorous composition. The metal phosphorous composition can comprise one or more of Si and Ti, for example. According to exemplary embodiments, the catalyst composition can comprise a solid substrate comprising one or more of $SiO_2$, $SiO_2$—$Al_2O_3$, and $TiO_2$. The solid substrate can be impregnated with a phosphoric acid. The phosphoric acid can be from about 8% (wt./wt.) to about 35% (wt./wt.) of the catalyst composition. According to a particular embodiment, the catalyst composition can comprise a solid substrate including $SiO_2$—$Al_2O_3$, and the solid substrate can be impregnated with a phosphoric acid from about 8% (wt./wt.) to about 30% (wt./wt.) of the catalyst composition. The catalyst composition can also include a solid substrate comprising $SiO_2$, and the solid substrate can be impregnated with phosphoric acid to a level of from about 29% (wt./wt.) to about 35% (wt./wt.) of the catalyst composition. Impregnation of these metal phosphorous catalysts can be performed by incipient wetness of an appropriate quantity of 85 wt % $H_3PO_4$ in deionized water to give the desired loading during impregnation. Following impregnation, the catalysts can be dried at 100° C. and used without further treatment. The performance of these catalysts is shown below in Table 2.

During this process, where the multihydric alcohol compound is glycerol, every mole of glycerol exposed to the catalyst composition can form at least about 0.4 moles of product composition. In accordance with another example, every mole of glycerol exposed to the catalyst composition can form from about 0.4 moles to about 0.99 moles of product composition. Where the product composition can include both acrolein and acetol, a ratio of acrolein to acetol and the product composition can be at least about 8:1 or from about 3.1 to 8.1.

In accordance with another embodiment, catalyst 34 can include a metal phosphate composition. The metal phosphate composition can include one or more elements from groups 2-7 and 9-12 of the periodic table of elements. The metal phosphate composition, for example, can include one or more of Cr, Mn, Fe, Co, Ni, Zn, La, Ca, Sr, Ba, Mo, Al, B, and Ru. The metal phosphate composition can be in the form of a metal dihydrogen phosphate, a metal hydrogen phosphate, or a metal phosphate. The metal phosphate composition can also include phosphoric acid. According to exemplary embodiments, the metal phosphate composition can include $MO_{0.33}H_{2.33}PO_4$ with M being one or more of Cr, Mn, Fe, Ru, Co, Ni, Zn, Ba, B, or La.

These metal phosphate composition catalysts can be prepared, for example, in a 200 mL beaker charged with metal nitrite and dissolved with a minimal amount of deionized water, for example. A 25 wt % solution of $(NH_4)_2HPO_4$ in deionized water can be prepared and an appropriate quantity of solution transferred to a small beaker. Ludox AS-40 can be placed in a graduated cylinder. With stirring, the ammonium phosphate and Ludox solutions can be poured concurrently into the nitrate solution, resulting in precipitation of metal

TABLE 2

Performance of supported phosphoric acid catalysts for glycerol dehydration at 300° C.

| wt % $H_3PO4$ | Catalyst Support | Contact Time (s) | % Carbon Balance | % Conv. | % Acrolein Yield | Acrolein Selectivity | Acetol Selectivity |
|---|---|---|---|---|---|---|---|
| 8 | $SiO_2$—$Al_2O_3$ | 0.25 | 74.49 | 81.47 | 48.28 | 0.594 | 0.095 |
| 20 | $SiO_2$—$Al_2O_3$ | 0.11 | 91.56 | 46.26 | 33.18 | 0.717 | 0.100 |
| 20 | $SiO_2$—$Al_2O_3$ | 0.06 | 99.72 | 17.26 | 14.80 | 0.857 | 0.126 |
| 25 | $Al_2O_3$ | 0.30 | 49.14 | 95.23 | 34.48 | 0.362 | 0.104 |
| 25 | $Al_2O_3$ | 0.30 | 41.76 | 94.68 | 27.98 | 0.296 | 0.089 |
| 30 | $SiO_2$—$Al_2O_3$ | 0.21 | 79.58 | 41.56 | 17.83 | 0.429 | 0.080 |
| 35 | $SiO_2$ | 0.12 | 84.29 | 83.49 | 58.44 | 0.700 | 0.112 |
| 35 | $SiO_2$ | 0.07 | 95.52 | 47.78 | 37.75 | 0.790 | 0.116 |
| 29* | $SiO_2$ | 0.24 | 93.83 | 99.17 | 80.48 | 0.812 | 0.126 |

*utilized $(NH_4)_2HPO_4$ as a catalyst precursor calcined at 350° C.

Contact times shorter than 4 seconds can be sufficient to effect dehydration of glycerol at 300° C. In accordance with some embodiments, greater than 90% glycerol dehydration can be realized with contact times of 300 milliseconds or less. Reactions performed at less than about 280° C. can form coke as a by-product. For contact times greater than 200 milliseconds, conversion ranged between 40% and 99%. Selectivities for acrolein and acetol using solid phosphoric acid catalysts have been reported to be 70% and 10%, respectively. A shown in FIG. 3, a linear correlation can exist between carbon balance and selectivity for both acrolein and acetol. Such an observation could possibly indicate missing carbon in the form of polymer, coke or formic and acetic acids, arising from decomposition of acrolein and acetol or other intermediate products.

phosphates. Stirring can be continued overnight and, depending on composition, sometimes results in a partial gelation. Excess water can then be removed on a rotary evaporator at 40 torr while employing a bath temperature of 60° C. The dried solids can be calcined in air for about 6 hours at 350° C. The calcined solids can then be crushed and sieved to a size appropriate for the reactor employed.

Referring again to FIG. 2, a multihydric alcohol compound such as glycerol can be provided from reactor reservoir 24 to reactor 22 having a metal phosphate catalyst composition utilized as catalyst 34. The multihydric alcohol compounds can be provided to this metal phosphate composition catalyst utilizing reactor temperatures between 250° C. and 340° C., with contact times of less than 500 milliseconds. Tables 3 and 4 below are exemplary of the data acquired utilizing these metal phosphate composition catalysts.

TABLE 3

Performance of supported metal phosphate-phosphoric acid catalysts for glycerol dehydration at 300° C.

| Metal | Contact Times (sec) | % Mass Balance | % Carbon Balance | % Conv. | % Acrolein Yield | Acrolein Selectivity | Acetol Selectivity |
|---|---|---|---|---|---|---|---|
| Ba | 0.25 | 97.06 | 98.67 | 99.78 | 84.28 | 0.845 | 0.142 |
| Cr | 0.24 | 90.69 | 84.33 | 30.41 | 12.38 | 0.407 | 0.078 |
| Mn | 0.23 | 97.88 | 93.35 | 99.88 | 80.43 | 0.805 | 0.128 |
| Fe | 0.25 | 102.60 | 96.97 | 99.49 | 83.07 | 0.835 | 0.135 |
| Co | 0.21 | 100.96 | 96.79 | 99.60 | 82.00 | 0.823 | 0.145 |
| Ni | 0.24 | 94.39 | 86.13 | 92.40 | 68.08 | 0.737 | 0.113 |
| Zn | 0.24 | 94.70 | 91.83 | 99.86 | 82.07 | 0.822 | 0.096 |
| La | 0.24 | 90.83 | 75.85 | 86.77 | 53.36 | 0.615 | 0.107 |
| Ru | 0.25 | 98.41 | 63.19 | 100.00 | 43.69 | 0.437 | 0.195 |
| Mo | 0.28 | 95.68 | 44.26 | 80.42 | 21.66 | 0.269 | 0.038 |

TABLE 4

Performance of supported metal phosphate-phosphoric acid catalysts for glycerol dehydration at 320° C.

| Metal | Contact Times (sec) | % Mass Balance | % Carbon Balance | % Conv. | % Acrolein Yield | Acrolein Selectivity | Acetol Selectivity |
|---|---|---|---|---|---|---|---|
| Ba | 0.25 | 81.17 | 74.29 | 93.46 | 59.56 | 0.637 | 0.088 |
| Mn | 0.24 | 90.69 | 89.28 | 95.01 | 74.88 | 0.79 | 0.10 |
| Fe | 0.23 | 86.71 | 82.28 | 24.75 | 6.06 | 0.245 | 0.039 |
| Zn | 0.24 | 95.68 | 90.85 | 99.58 | 79.69 | 0.800 | 0.108 |
| Co | 0.25 | 89.86 | 91.40 | 98.73 | 79.51 | 0.81 | 0.11 |
| Mo | 0.29 | 97.98 | 48.89 | 87.30 | 31.69 | 0.363 | 0.052 |
| Ni | 0.24 | 96.26 | 87.45 | 96.44 | 73.81 | 0.765 | 0.105 |

Quantitative glycerol conversion can be effected in most catalysts using contact times of less than 250 milliseconds. Acrolein selectivities typically exceeded 80% with catalysts incorporating metals of the middle transition series and acetol selectivities consistently ranged between 10% and 20%. Coke formation can be observed with the most active catalysts.

Figure 4:
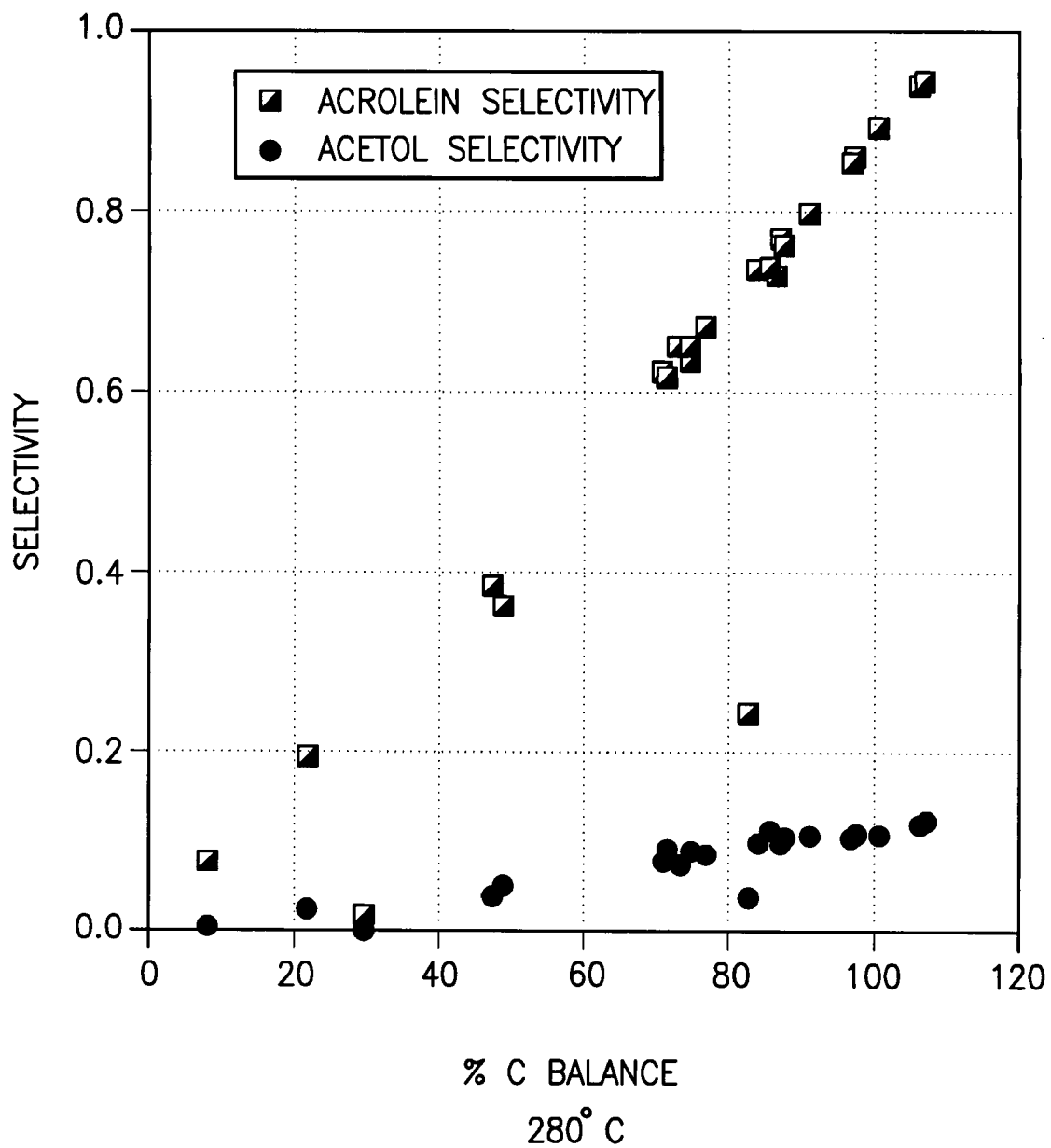
FIG. 4 is a plot of data acquired utilizing an embodiment of the disclosure.
Figure 5:
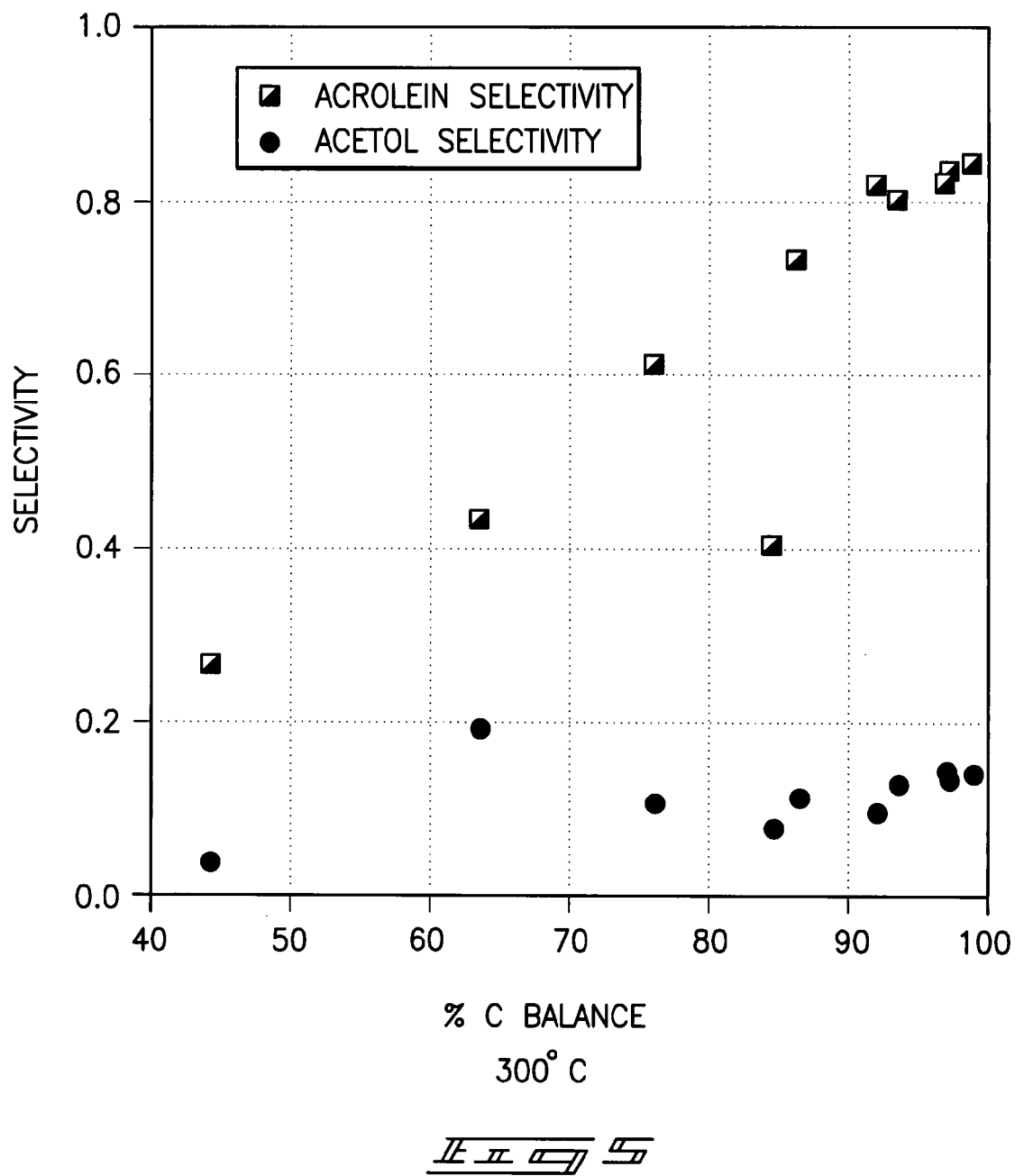
FIG. 5 is a plot of data acquired utilizing an embodiment of the disclosure.
Figure 6:
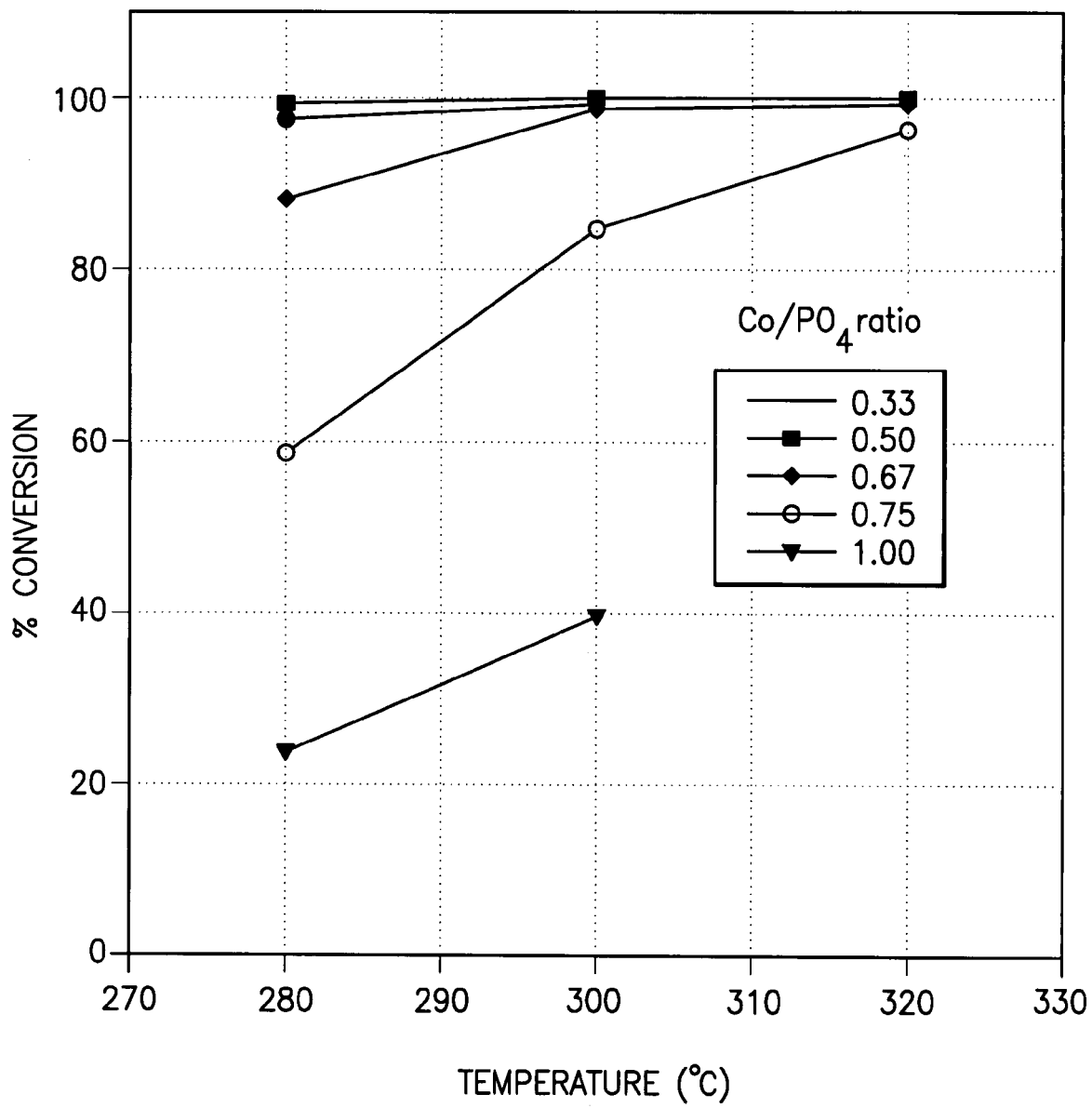
FIG. 6 is a plot of data acquired utilizing an embodiment of the disclosure.

Referring to FIGS. 4 and 5, it can be observed that acrolein and/or acetol selectivities correlate with carbon balance.

Catalyst compositions can affect glycerol conversion to 50% or greater. For example, when 5% silica alumina is utilized at 300° C., a 41% glycerol conversion can be realized. This silica alumina material utilized in combination with $CO_2$ facilitated a glycerol conversion more than double, though acrolein yield can be increased which can indicate nonselectivity from contributions of carbonic acid catalysis. Increasing reaction temperature can increase conversion for active catalysts such as zirconia though selectivity may not improve with increasing reaction temperature.

During the process of exposing the multihydric alcohol compound to this solid substrate catalyst, every mole of glycerol exposed to the catalyst composition can form at least about 0.1 moles of product composition, with the product composition including acrolein and acetol, for example. Every mole of glycerol exposed to the catalyst composition can also form from about 0.1 moles to about 0.99 moles of product composition. Where the product composition comprises both acrolein and acetol, exposing glycerol to this solid substrate composition can provide a ratio of acrolein to acetol within the product composition of at least about 9:1. As an example, the ratio of acrolein to acetol within the product composition can be from about 1.2 to about 9.1.

As part of the standard protocol for screening, exposure of the multihydric alcohol compound to catalysts can be performed at two or three temperatures in addition to 300° C. As an example, data for a series of Co catalysts (varying $Co/PO_4$ ratio, see Tables 5-14) are illustrated graphically in FIG. 6.

TABLE 5

Effect of reaction temperature on selectivity and conversion for $Co_{0.33}H_{2.33}PO_4$

| Glycerol Feed Concentration % | Temp (° C.) | Contact Times (sec) | % C balance | % Conv. | % Acrolein Yield | Acrolein Selectivity | Acetol Selectivity |
|---|---|---|---|---|---|---|---|
| 17 | 250 | 0.27 | 92.21 | 96.66 | 79.60 | 0.82 | 0.10 |
| 17 | 260 | 0.27 | 95.78 | 99.87 | 85.25 | 0.85 | 0.10 |
| 17 | 270 | 0.26 | 99.23 | 98.92 | 87.30 | 0.88 | 0.11 |
| 30 | 280 | 0.24 | 98.46 | 97.45 | 85.03 | 0.87 | 0.11 |

TABLE 5-continued

Effect of reaction temperature on selectivity and conversion for $Co_{0.33}H_{2.33}PO_4$

| Glycerol Feed Concentration % | Temp (° C.) | Contact Times (sec) | % C balance | % Conv. | % Acrolein Yield | Acrolein Selectivity | Acetol Selectivity |
|---|---|---|---|---|---|---|---|
| 30 | 300 | 0.21 | 96.79 | 99.60 | 82.00 | 0.82 | 0.14 |
| 30 | 320 | 0.24 | 100.88 | 99.61 | 83.90 | 0.84 | 0.17 |

Over two glycerol feed concentration ranges (which permit comparisons at constant conversion and contact time), selectivities for acetol can increase monotonically with increasing reaction temperature. The acrolein selectivity can appear to increase up to 270° C. and then begin decreasing up to 320° C. This can be consistent with the measured acrolein selectivity being very strongly correlated with carbon balance. Temperature can control both the intrinsic reaction kinetics (inherent mechanistic selectivities of a reaction) and product decomposition rates. An assessment of the propensity to form acrolein over acetol (intrinsic selectivity) can be made with extrapolation to 100% carbon balance (i.e., with the assumption of no product decomposition). To accomplish this assessment for example, the selectivity data for acrolein and acetol can be divided by the fractional carbon balances. The results of this example data calculation are provided in Table 6 below.

TABLE 6

Effect of reaction temperature on intrinsic selectivities $Co_{0.33}H_{2.33}PO_4$

| Glycerol Feed Concentration % | Temp (° C.) | % C balance | Acrolein Selectivity | Acetol Selectivity | Intrinsic Acrolein Selectivity | Intrinsic Acetol Selectivity |
|---|---|---|---|---|---|---|
| 17 | 250 | 92.21 | 0.820 | 0.100 | 0.889 | 0.108 |
| 17 | 260 | 95.78 | 0.850 | 0.100 | 0.887 | 0.104 |
| 17 | 270 | 99.23 | 0.880 | 0.110 | 0.887 | 0.111 |
| 30 | 280 | 98.46 | 0.870 | 0.110 | 0.884 | 0.112 |
| 30 | 300 | 96.79 | 0.820 | 0.140 | 0.847 | 0.145 |
| 30 | 320 | 100.88 | 0.840 | 0.170 | 0.833 | 0.169 |

Referring to Table 6, the acrolein selectivity is highest at the lower temperatures and decreases monotonically with increasing temperature with what appears to be the exact opposite trend observed for acetol. Similar results are obtained when data for the barium congener are treated analogously (Table 7).

TABLE 7

Effect of reaction temperature on intrinsic selectivities of $Ba_{0.33}H_{2.33}PO_4$

| T (° C.) | Carbon Balance | Acrolein Selectivity | Acetol Selectivity | Intrinsic Acrolein Selectivity | Intrinsic Acetol Selectivity |
|---|---|---|---|---|---|
| 250 | 91.86 | 0.794 | 0.101 | 0.865 | 0.110 |
| 260 | 90.82 | 0.803 | 0.104 | 0.885 | 0.115 |
| 270 | 97.30 | 0.855 | 0.118 | 0.879 | 0.121 |
| 280 | 74.29 | 0.637 | 0.088 | 0.858 | 0.118 |
| 300 | 98.67 | 0.845 | 0.142 | 0.856 | 0.144 |
| 320 | 103.62 | 0.89 | 0.15 | 0.855 | 0.145 |

Figure 7:
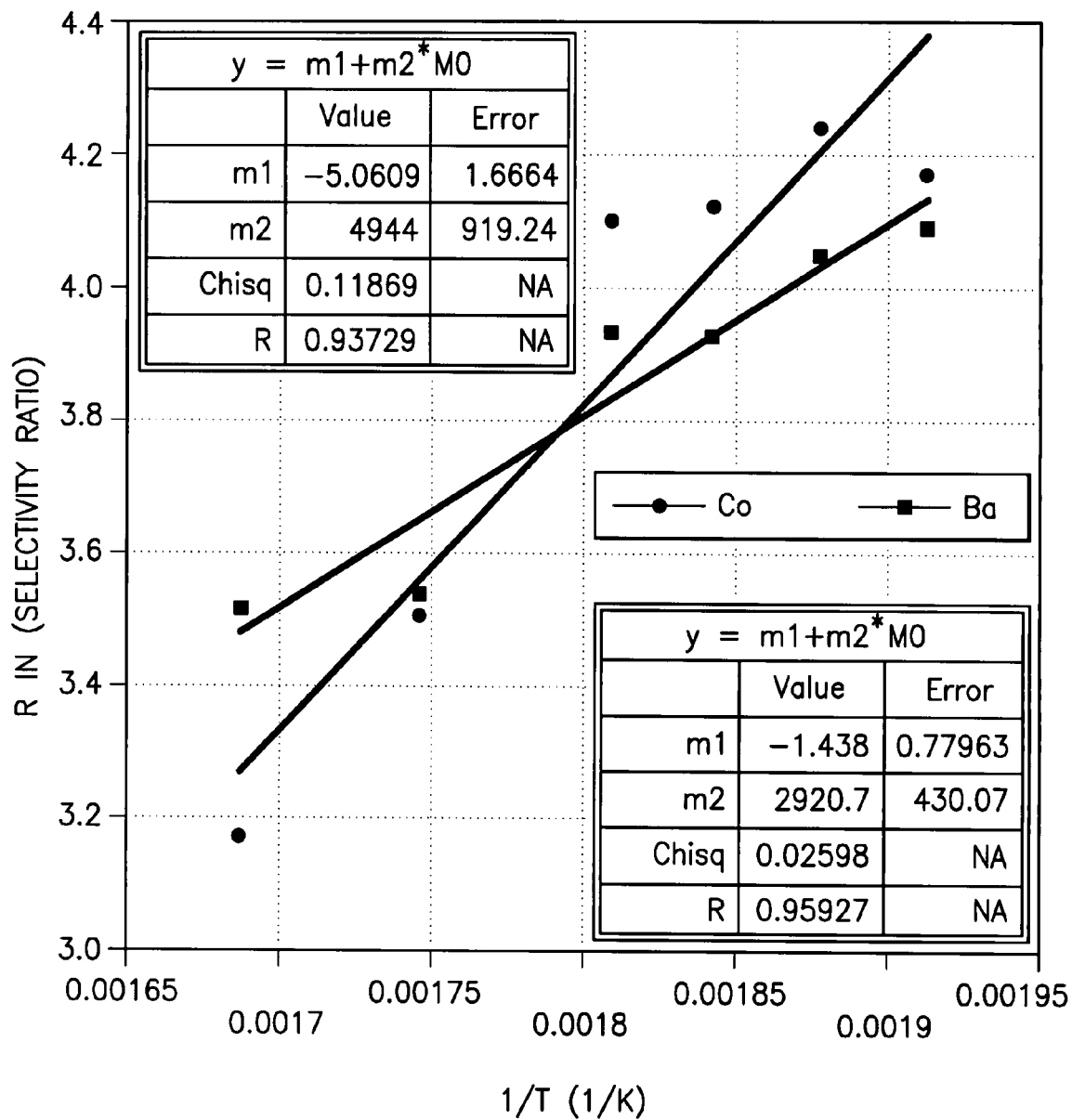
FIG. 7 is a plot of data acquired utilizing an embodiment of the disclosure.

Referring to Table 7, the ratio of intrinsic selectivities can be related to the differences in the activation energies for the two transition states leading to acrolein and acetol from glycerol. By plotting R ln(ratio) versus (1/T), a linear relationship results, the slope of which represents the difference in transition state energies leading to acrolein and acetol. FIG. 7 shows such a plot using data from Tables 6 and 7. While some experimental scatter leads to somewhat less than desirable R-factors of 0.93 and 0.95 for Co and Ba, respectively, the data allow an estimation of the difference in activation energies for acrolein and acetol formation. For the barium catalyst, a value of $2.93 \pm 0.43$ kcal $mol^{-1}$ is measured as the difference in the transition state energies of acrolein and acetol. For the cobalt catalyst, the calculated value is $4.94 \pm 0.92$ kcal $mol^{-1}$.

TABLE 8

Calculated intrinsic selectivities for $Co_{0.33}H_{2.33}PO_4$ and $Ba_{0.33}H_{2.33}PO_4$ as a function of temperature.

| T (° C.) | Intrinsic Acrolein Selectivity (Co) | Intrinsic Acetol Selectivity (Ba) |
|---|---|---|
| 100 | 0.984 | 0.961 |
| 125 | 0.976 | 0.951 |
| 150 | 0.965 | 0.940 |
| 175 | 0.953 | 0.928 |
| 200 | 0.938 | 0.915 |
| 225 | 0.920 | 0.902 |
| 250 | 0.901 | 0.889 |
| 275 | 0.880 | 0.876 |
| 300 | 0.857 | 0.863 |
| 325 | 0.834 | 0.850 |
| 350 | 0.809 | 0.837 |
| 375 | 0.784 | 0.824 |
| 400 | 0.759 | 0.811 |
| 425 | 0.734 | 0.799 |
| 450 | 0.709 | 0.787 |

Referring to Table 8, catalysts can be prepared in the conventional manner by precipitation of metal phosphate in the presence of colloidal silica. The catalysts can maintain phosphate weight ratios of previous catalyst studies (phosphate:silica=0.29) but varied the metal-phosphate stoichiometry from the original 0.33:1 M:$PO_4$ ratio by increasing the metal nitrate precursor loading. Catalysts with Co:$PO_4$ ratios of 0.50, 0.67, 0.75 and 1.00 can be prepared in this manner and calcined at 350° C. for 6 hours prior to screening for comparison to the original 0.33:1 composition. Similarly, catalysts with Ba:$PO_4$ ratios of 0.50, 0.75, 1.00 and 1.50 can be prepared for comparison with the original 0.33:1 composition. The multihydro alcohol compound glycerol was then exposed to the catalyst composition at temperatures of 280, 300 and 320° C. Data for both catalysts are provided in Tables 9-14 below.

TABLE 9

Effect of metal-phosphate ratio on Co catalyst performance at 280° C.

| Co/PO$_4$ mole ratio | % C balance | % Glycerol Conversion | % Acrolein Yield | Acrolein Selectivity | Acetol Selectivity | Intrinsic Acrolein Selectivity |
|---|---|---|---|---|---|---|
| 0.33 | 98.46 | 97.45 | 85.03 | 0.87 | 0.11 | 0.884 |
| 0.5 | 97.32 | 99.5 | 86.16 | 0.87 | 0.11 | 0.894 |
| 0.67 | 89.96 | 88.31 | 68.94 | 0.78 | 0.11 | 0.867 |
| 0.75 | 87.16 | 58.8 | 40.42 | 0.69 | 0.09 | 0.792 |
| 1 | 93.29 | 23.61 | 14.66 | 0.62 | 0.09 | 0.665 |

TABLE 10

Effect of metal-phosphate ratio on Co catalyst performance at 300° C.

| Co/PO$_4$ mole ratio | % C balance | % Glycerol Conversion | % Acrolein Yield | Acrolein Selectivity | Acetol Selectivity | Intrinsic Acrolein Selectivity |
|---|---|---|---|---|---|---|
| 0.33 | 96.79 | 99.6 | 82 | 0.82 | 0.14 | 0.847 |
| 0.5 | 104.21 | 99.82 | 92.21 | 0.92 | 0.12 | 0.883 |
| 0.67 | 94.96 | 98.87 | 81.23 | 0.82 | 0.13 | 0.864 |
| 0.75 | 98.33 | 84.91 | 72.61 | 0.86 | 0.13 | 0.875 |
| 1 | 92.84 | 39.23 | 27.5 | 0.7 | 0.12 | 0.754 |

TABLE 11

Effect of metal-phosphate ratio on Co catalyst performance at 320° C.

| Co/PO$_4$ mole ratio | % C balance | % Glycerol Conversion | % Acrolein Yield | Acrolein Selectivity | Acetol Selectivity | Intrinsic Acrolein Selectivity |
|---|---|---|---|---|---|---|
| 0.33 | 100.88 | 99.61 | 83.9 | 0.84 | 0.17 | 0.833 |
| 0.5 | 100.4 | 99.76 | 87.15 | 0.87 | 0.13 | 0.867 |
| 0.67 | 104.46 | 99.55 | 88.79 | 0.89 | 0.15 | 0.852 |
| 0.75 | 98.39 | 96.39 | 81.02 | 0.84 | 0.14 | 0.854 |

TABLE 12

Effect of metal-phosphate ratio on Ba catalyst performance at 280° C.

| Ba/PO$_4$ mole ratio | % C balance | % Glycerol Conversion | % Acrolein Yield | Acrolein Selectivity | Acetol Selectivity | Intrinsic Acrolein Selectivity |
|---|---|---|---|---|---|---|
| 0.33 | 98.67 | 99.78 | 84.28 | 0.845 | 0.142 | 0.856 |
| 0.5 | 49.51 | 92.56 | 36.79 | 0.397 | 0.057 | 0.803 |
| 0.75 | 44.87 | 74.88 | 17.20 | 0.230 | 0.034 | 0.512 |
| 1.0 | 52.93 | 0.00 | 0.00 | 0.000 | 0.000 | 0.000 |
| 1.5 | 55.12 | 0.00 | 0.00 | 0.000 | 0.000 | 0.000 |

TABLE 13

Effect of metal-phosphate ratio on Ba catalyst performance at 300° C.

| Ba/PO$_4$ mole ratio | % C balance | % Glycerol Conversion | % Acrolein Yield | Acrolein Selectivity | Acetol Selectivity | Intrinsic Acrolein Selectivity |
|---|---|---|---|---|---|---|
| 0.33 | 74.29 | 93.46 | 59.56 | 0.637 | 0.088 | 0.858 |
| 0.5 | 48.25 | 87.56 | 31.49 | 0.360 | 0.049 | 0.745 |
| 0.75 | 49.51 | 66.25 | 13.72 | 0.207 | 0.031 | 0.418 |

TABLE 13-continued

Effect of metal-phosphate ratio on Ba catalyst performance at 300° C.

| Ba/PO$_4$ mole ratio | % C balance | % Glycerol Conversion | % Acrolein Yield | Acrolein Selectivity | Acetol Selectivity | Intrinsic Acrolein Selectivity |
|---|---|---|---|---|---|---|
| 1.0 | 60.30 | 0.00 | 0.00 | 0.000 | 0.000 | 0.000 |
| 1.5 | 57.42 | 0.00 | 0.00 | 0.000 | 0.000 | 0.000 |

TABLE 14

Effect of metal-phosphate ratio on Ba catalyst performance at 320° C.

| Ba/PO$_4$ mole ratio | % C balance | % Glycerol Conversion | % Acrolein Yield | Acrolein Selectivity | Acetol Selectivity | Intrinsic Acrolein Selectivity |
|---|---|---|---|---|---|---|
| 0.33 | 103.62 | 99.85 | 88.42 | 0.89 | 0.15 | 0.855 |
| 0.5 | 46.58 | 79.20 | 22.16 | 0.280 | 0.046 | 0.601 |
| 1.5 | 56.12 | 0.00 | 0.00 | 0.000 | 0.000 | 0.000 |

Referring to Tables 9-14, it can be observed that for all compositions of Co and Ba, increasing temperature can lead to increased conversion, decreased acrolein selectivity, and increased acetol selectivity, as was observed with the parent 0.33:1 M:PO$_4$ ratio compositions. The effect of the metal:phosphate ratio at a particular temperature may depend on the metal employed. For cobalt catalysts, activity and selectivity diminished with an increasing Co:PO$_4$ ratio with the optimum ratio for both activity and selectivity observed at 0.5:1. This composition, assuming a statistically equilibrated mixture, can correspond to a bulk stoichiometry of Co(H$_2$PO$_4$)$_2$. For the barium catalysts, compositions with Ba:PO$_4$ ratios less than 1.0 can be active with the original 0.33:1 Ba:PO$_4$ composition providing the highest activity and selectivity. For compositional ratios of 1.0 and 1.5, bulk stoichiometries of BaHPO$_4$ and Ba$_3$(PO$_4$)$_2$, respectively, can result. With decreasing metal:phosphate ratios, increasing acidity can result with dihydrogenphosphates representing bulk stoichiometries for divalent metals at ratios of 0.5 and mixtures of phosphoric acid and metal dihydrogenphosphate complexes at lesser ratios. Thus, while monohydrogenphosphate complexes of cobalt (Co:PO$_4$=1.0) may appear to contain enough acidity to effect glycerol dehydration, barium complexes require some degree of dihydrogenphosphate for effectiveness. Taking precipitation kinetics into account during catalyst preparation, while a divalent M:PO$_4$ ratio of 0.5 would correspond to a bulk stoichiometry of M(H$_2$PO$_4$)$_2$, the composition may in fact comprise equal quantities of H$_3$PO$_4$ and MHPO$_4$ when accounting for the low solubility of metal phosphate salts. Therefore, unless equilibration of acid and basic sites occurs post-precipitation (e.g., during calcinations), it may be that working catalysts exhibit a distribution of compositions based on metal identity and stoichiometry.

In compliance with the statute, this disclosure has been provided in language more or less specific as to structural and methodical features. It is to be understood, however, that the disclosure is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

What is claimed is:

1. A chemical production process comprising exposing a reactant composition to a catalyst composition to form a product composition, wherein:

the reactant composition comprises glycerol;

the catalyst composition comprises a metal phosphate composition, the metal phosphate composition comprising one or more of Cr, Mn, Co, Ni, La, Ca, Sr, Ba, Mo, B, and Ru; wherein the catalyst composition comprises a solid substrate comprising one or more of $SiO_2$, $SiO_2$—$Al_2O_3$, C, and $TiO_2$ the solid substrate being impregnated with phosphoric acid, and the phosphoric acid is from about 8% (wt./wt.) to about 35% (wt./wt.) of the catalyst composition; and the product composition comprises acrolein.

2. The chemical production process of claim 1 wherein at least a portion of the product composition is later utilized as a reactant.

3. The chemical production process of claim 1 wherein the metal phosphate composition comprises one or more or a metal dihydrogen phosphate, a metal hydrogen phosphate, and a metal phosphate.

4. The chemical production process of claim 1 wherein the metal phosphate composition comprises phosphoric acid.

5. The chemical production process of claim 1 wherein the metal phosphate composition comprises $M_{0.33}H_{2.33}PO_4$, wherein M is one of Cr, Mn, Fe, Ru, Co, Ni, Ba, B, or La.

6. The chemical production process of claim 1 wherein the ratio of metal to phosphate in the metal phosphate composition is at least 0.33:1.

7. The chemical production process of claim 1 wherein the ratio of metal to phosphate in the metal phosphate composition is from about 0.33:1 to about 1.5:1.

8. The chemical production process of claim 1 wherein the catalyst composition further comprises one or more of Si and Ti.

9. The chemical production process of claim 8 wherein the phosphoric acid is from about 8% (wt./wt.) to about 30% (wt./wt.) of the catalyst composition.

10. The chemical production process of claim 8 wherein the phosphoric acid is from about 29% (wt./wt.) to about 35% (wt./wt.) of the catalyst composition.

11. The chemical production process of claim 1 wherein every mole of glycerol exposed to the catalyst composition forms at least about 0.4 moles of product composition.

12. The chemical production process of claim 1 wherein every mole of glycerol exposed to the catalyst composition forms about 0.4 moles to about 0.99 moles of product composition.

13. The chemical production process of claim 1 wherein the product composition comprises both acrolein and acetol.

14. The chemical production process of claim 13 wherein a ratio of acrolein to acetol is at least about 8:1.

15. The chemical production process of claim 13 wherein a ratio of acrolein to acetol is from about 3:1 to about 8:1.

* * * * *

UNITED STATES PATENT AND TRADEMARK OFFICE
CERTIFICATE OF CORRECTION

| | | |
|---|---|---|
| PATENT NO. | : 7,872,159 B2 | Page 1 of 1 |
| APPLICATION NO. | : 11/895362 | |
| DATED | : January 18, 2011 | |
| INVENTOR(S) | : Thomas H. Peterson et al. | |

It is certified that error appears in the above-identified patent and that said Letters Patent is hereby corrected as shown below:

(56) References Cited – Replace "WO US2008/074090 5/2009" with --WO PCT/US2008/074090 5/2009--

Column 5, line 61 – Replace "A shown" with --As shown--

Column 6, line 22 – Replace "$MO_{0.33}H_{2.33}PO_4$" with --$M_{0.33}H_{2.33}PO_4$--

Signed and Sealed this

Seventeenth Day of April, 2012

David J. Kappos
*Director of the United States Patent and Trademark Office*